United States Patent [19]

Schmitt

[11] 4,217,253

[45] Aug. 12, 1980

[54] MIXTURE OF 3-METHYL-1-PHENYL-PENTANOL-5 OR ITS ISOMERS AND BUTANOYL CYCLOHEXANE DERIVATIVES

[75] Inventor: Frederick L. Schmitt, Holmdel, N.J.

[73] Assignee: International Flavors & Fragrances Inc., New York, N.Y.

[21] Appl. No.: 57,357

[22] Filed: Jul. 13, 1979

Related U.S. Application Data

[62] Division of Ser. No. 949,140, Oct. 6, 1978.

[51] Int. Cl.$^2$ .......................... C11B 9/00; A61K 7/46
[52] U.S. Cl. ................................ 252/522 R; 252/108; 252/173; 252/368; 424/76; 424/64; 424/358; 424/70; 424/73; 252/89.1
[58] Field of Search ......................... 252/522; 260/598

[56] References Cited

U.S. PATENT DOCUMENTS

| | | | |
|---|---|---|---|
| 3,946,078 | 3/1976 | Rautenstrauch et al. | 252/522 R |
| 3,959,508 | 5/1976 | Pittet et al. | 252/522 R |
| 3,996,290 | 12/1976 | Tavares et al. | 252/522 R |
| 4,028,279 | 6/1977 | Van Ouwerkerk | 260/598 |

Primary Examiner—Veronica O'Keefe
Attorney, Agent, or Firm—Arthur L. Liberman

[57] ABSTRACT

Processes and compositions are described for the use in perfume aroma augmenting, modifying, altering and enhancing compositions and as perfume, cologne and perfumed article aroma imparting materials of mixtures of 3-methyl-1-phenyl-pentanol-5 and one or more butanoyl cyclohexane derivatives.

1 Claim, No Drawings

MIXTURE OF 3-METHYL-1-PHENYL-PENTANOL-5 OR ITS ISOMERS AND BUTANOYL CYCLOHEXANE DERIVATIVES

This is a divisional of application Ser. No. 949,140, filed Oct. 6, 1978.

BACKGROUND OF THE INVENTION

The present invention relates to mixtures of 3-methyl-1-phenyl-pentanol-5 and one or more butanoyl cyclohexane derivatives defined according to the following structures:

1. Structures of butanoyl cyclohexane derivatives:

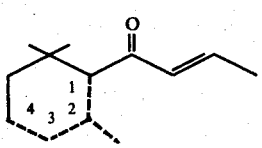

(generic structure) wherein one of the dashed lines is a carbon-carbon double bond or two of the dashed lines is a carbon-carbon double bond but that when two of the dashed lines represents a carbon-carbon double bond the carbon-carbon double bonds are conjugated.

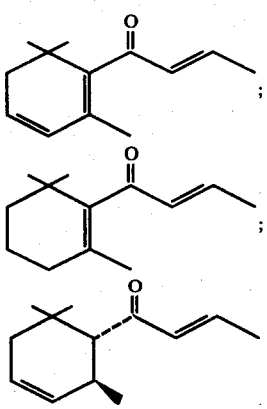

(wherein the dashed line represents a configuration of the butenoyl moiety "trans" with respect to the methyl moiety at the "two" position on the cyclohexene ring).

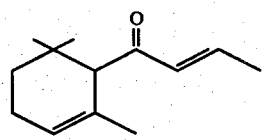

2. 3-Methyl-1-phenyl-pentanol-5:

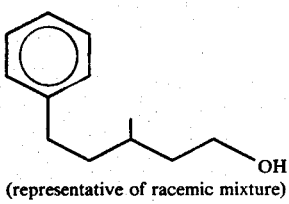

(representative of racemic mixture)

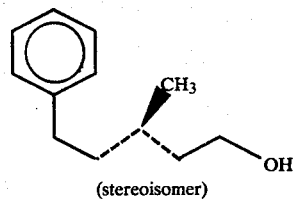

(stereoisomer)

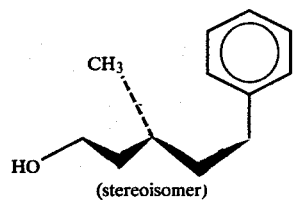

(stereoisomer)

There has been considerable work performed relating to substance which can be used to impart (or alter, modify or enhance) fragrances to (or in) perfumed compositions, perfumes or perfumed articles. These substances are used to diminish the use of natural materials, some of which may be in short supply and/or to provide more uniform properties in the finished product. Woody, rosey, green and earthy notes are desirable in many types of perfume compositions, perfumes and perfumed articles.

U.S. Pat. No. 4,028,279 entitled "Novel Fragrance Compositions Containing 2,6,6-Trimethyl-1-Cyclohexene-1-yl Acetaldehyde and Phenyl $C_6$ Ketone" relates to mixtures of (i) either or both of the phenyl $C_6$ ketones, 2,5-dimethyl-5-phenylhexanone-4 and 2,5-dimethyl-5-phenylhexen-1-one-3 and (ii) 2,2,6-trimethyl-1-cyclohexen-1-yl acetaldehyde used to alter, modify, enhance or impart aromas in or to perfumes, perfume compositions and/or perfumed articles. It is disclosed in said U.S. Pat. No. 4,028,279 that such perfume compositions containing such mixtures have intense rosey aromas with woody, green and earthy notes. The structure of the phenyl $C_6$ ketones disclosed in U.S. Pat. No. 4,028,279 is:

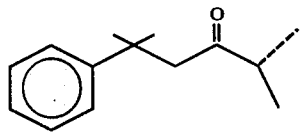

the structure of the betacyclohomocitral used in U.S. Pat. No. 4,028,279 is:

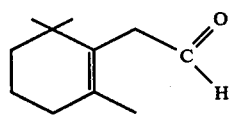

wherein the dashed line may be either a carbon-carbon single bond or a carbon-carbon double bond.

In U.S. Pat. No. 3,595,508, issued on May 25, 1976 mixtures of (i) 2,2,6-trimethyl-1-cyclohexen-1-yl acetaldehyde and (ii) 2,6,6-trimethyl crotonyl-1,3-cyclohexadiene having the structure:

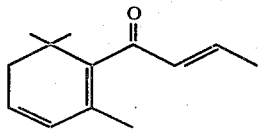

are indicated to produce in perfumes, rosey, woody, camphoraceous, green and earthy notes.

Nothing in the prior art including U.S. Pat. Nos. 3,959,508 and 4,028,279 imply or state that such mixtures as are disclosed and claimed in the instant case can be used to enhance and extend the specific rose nuances of butanoyl cyclohexane derivatives having the generic structure:

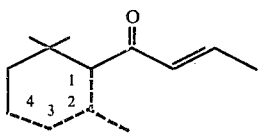

THE INVENTION

It has now been discovered that novel perfume compositions and perfumes having extended long-lasting highly intense and natural-like rosey notes and novel perfumed articles having extended long-lasting highly intense rosey aromas with woody, green and earthy notes may be provided by the utilization of mixtures of (i) one or more butanoyl cyclohexane derivatives having the structure:

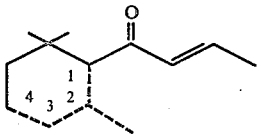

wherein one or two of the dashed lines is a carbon-carbon double bond and the other of the dashed lines are carbon-carbon single bonds with the proviso that if two of the dashed lines are carbon-carbon double bonds the carbon-carbon-carbon double bonds are conjugated and (ii) 3-methyl-1-phenyl-pentanol-5 racemic mixtures or individual stereoisomers having one of the structures:

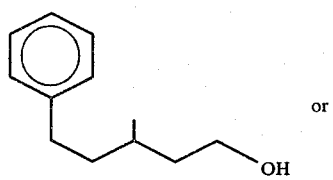

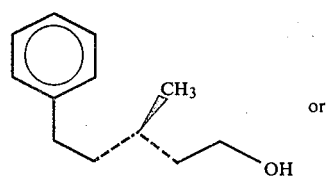

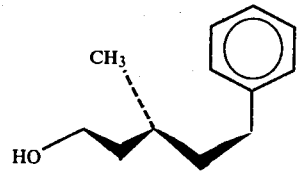

In perfumes, perfumed articles such as soaps and detergents, optical brightener compositions and fabric softeners (for example fabric softener compositions for clothes dryer), perfume compositions and colognes.

It has been discovered by us that the organoleptic effect obtained when using the combination of mixtures of 3-methyl-1-phenyl-pentanol-5 and one or more butanoyl cyclohexane derivatives is more than merely additive of the individual organoleptic properties of the 3-methyl-1-phenyl-pentanol-5 compound taken alone or in combination and the butanoyl cyclohexane derivatives (taken alone or taken in combination with one another); that the effect is described as synergistic.

The 3-methyl-1-phenyl-pentanol-5 described as having one of the structures:

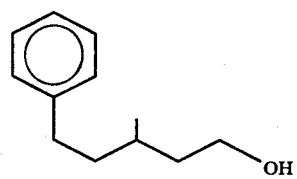

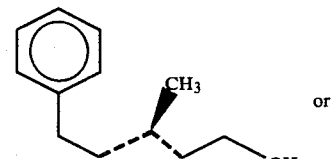

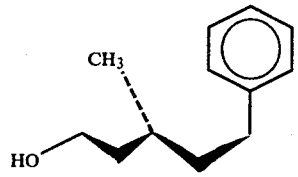

may be prepared according to the procedure described by Rupe Hirschmann and Werdenberg at Helv. 18 [1935] pages 535–542 (abstracted at Beilstein E III 6 1997, H 6,551).

Methods for preparing the butanoyl cyclohexane derivatives used in our invention are described in Swiss Pat. No. 520,479, issued on May 12, 1972 as well as application for United States Letters Patent, Ser. No. 851,727, filed on Nov. 15, 1977.

Contemplated within the scope of our invention are weight ratios of butanoyl cyclohexane derivative having the generic structure:

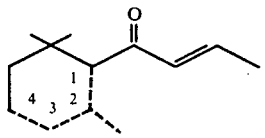

3-Methyl-1-phenyl-pentanol-5 of from about $1\times10^{-7}$:1 up to about 0.1:1. It is however preferable in the practice of our invention to use weight ratios of butanoyl cyclohexane derivative: 3-methyl-1-phenyl-pentanol-5 of from about $1\times10^{-7}$:1 up to about $5\times10^{-3}$:1.

When the mixtures of 3-methyl-1-phenyl-pentanol-5 and one or more butanoyl cyclohexane derivatives of our invention is used as a perfume aroma adjuvant, the nature of the co-ingredients included with the said mixture of 3-methyl-1-phenyl-pentanol-5 and one or more butanoyl cyclohexane derivatives in formulating the product composition will also serve to alter the organoleptic characteristics of any ultimate perfumed article treated therewith.

As used herein the terms "alter" and "modify" in their various forms mean supplying or imparting a perfume aroma character or note to otherwise bland substances or augmenting the existing aroma characteristic where a natural aroma is deficient in some regard or supplementing the existing aroma impression to modify its quality, character or aroma.

As used herein the term "enhance" is intended to mean the intensification (without effecting a change in kind or quality of aroma) of one or more aroma nuances and their organoleptic impression of a perfume, perfume composition or one or more perfumed articles.

The mixture of 3-methyl-1-phenyl-pentanol-5 and one or more butanoyl cyclohexane derivatives of our invention and one or more auxilliary perfume ingredients, including for example alcohols other than the 3-methyl-1-phenyl-pentanol-5 of mixture of our invention, aldehydes, ketones other than the butanoyl cyclohexane derivatives of the mixture of our invention, nitriles, esters, lactones, natural essential oils and synthetic essential oils may be admixed so that the combined odors of the individual components produce a pleasant and desired fragrance, particularly and preferably in the rose or rose muguet and other floral fragrances. It is to be understood that such additional adjuvants are to be organoleptically compatible with each of said 3-methyl-1-phenyl-pentanol-5 and one or more of said butanoyl cyclohexane derivatives of our invention and further that such adjuvants are to be nonreactive under use conditions at room temperature and storage conditions with the said 3-methyl-1-phenyl-pentanol-5 and the butanoyl cyclohexane derivatives of the mixture of our invention.

Such perfume compositions usually contain (a) the main note or the bouquet or foundation stone of the compositions (b) modifiers which round off and accompany the main note; (c) fixatives which include odorours substances which lend a particular note to the perfume throughout all stages of evaporation and substances with which retard evaporation and (d) topnotes which are usually low boiling, fresh smelling materials.

In perfume compositions, the individual components who will contribute their particular olfactory characteristic; and these individual components will also alter or modify or enhance the overall effect of the perfume composition. Thus, the mixture of 3-methyl-1-phenyl-pentanol-5 and one or more butanoyl cyclohexane derivatives can be used to alter, augment or enhance the aroma characteristics of a perfume composition for example by utilizing or moderating the olfactory reaction contributed by one or more other ingredients in the composition.

The amount of mixture of 3-methyl-1-phenyl-pentanol-5 and one or more butanoyl cyclohexane derivatives of our invention which will be effective in perfume composition depends on many factors including the other ingredients, their amounts and the effects which are desired. It has been found that perfume compositions containing as little as 0.01% of the mixture of 3-methyl-1-phenyl-pentanol-5 and one or more butanoyl cyclohexane derivatives and even less (e.g. 0.005%) can be used to impart a rosey or muguet aroma to cosmetics and other produces including fabric softener articles used in clothes dryers. The amount employed can range up to 10% of the fragrance components and will depend on considerations of cost, nature of the end product, the effect desired on the finished product and the particular fragrance sought.

The mixture of 3-methyl-1-phenyl-pentanol-5 and one or more butanoyl cyclohexane derivatives is useful taken alone or in perfume compositions as an olfactory component in anionic, cationic and nonionic detergents and soaps, space odorants and deodorants, perfumes, colognes, toilet water, bath preparations such as bath oils and bath solids; hair preparations such as lacquers, brilliantines, pomades and shampoos; costmetic preparations, such as creams, deodorants, hand lotions and sun screens; powders, such as talcs, dusting powders, face powders and the like. When used as an olfactory component as little as 0.25% of the mixture of 3-methyl-1-phenyl-pentanol-5 and one or more butanoyl cyclohexane derivatives will suffice to impart a muguet rose note to petitgrain formulations. Generally, no more than 3% of the mixture of 3-methyl-1-phenyl-pentanol-5 and one or more butanoyl cyclohexane derivatives based on the ultimate end product is required in the perfume composition.

In addition, the perfume composition or fragrance composition of our invention can contain a vehicle, or carrier for the mixture of 3-methyl-1-phenyl-pentanol-5 and one or more butanoyl cyclohexane derivatives. The vehicle can be a liquid such as a nontoxic alcohol (e.g. 95% food grade ethanol), a nontoxic glycol (e.g. propylene glycol) or the like. The carrier can also be an absorbent sold, such as gum (e.g. gum arabic) or components for encapsulating the composition (such as gelatin) as by means of coacervation.

The following examples are illustrative and the invention is to be considered to be restricted thereto only as indicated in the appended claims. All parts and percentages given herein are by weight unless otherwise specified.

EXAMPLE I

Rose Formulation

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenyl Ethyl Alcohol | 12.0 |
| Terpinenol | 5.0 |
| Linalyl Acetate | 1.5 |
| Citronellyl Acetate | 15.0 |
| Geranyl Acetate | 10.0 |
| Eugenol | 33.0 |
| Citral | 15.0 |
| Phenyl Ethyl Acetate | 20.0 |
| Rose Oxide | 8.0 |
| Guaiacol | 30.0 |
| l-citronellal | 90.0 |

| Ingredients | Parts by Weight |
|---|---|
| Neryl Acetate | 3.0 |
| Clove Bud Oil | 1.0 |
| Cadinene | 2.0 |
| Guaiene | 1.0 |
| Gum Turpentine | 12.0 |
| Alpha-pinene | 1.0 |
| Myrcene | 5.0 |
| Limonene | 2.0 |
| p-cymene | 1.0 |
| | 687.5 |

To the foregoing formulation 30 parts by weight of a 0.1% solution of 3-methyl-1-phenyl-pentanol-5 in diethyl phthalate and 15 parts by weight of a 0.01% solution of damascenone in diethyl phthalate is added. The resultant mixture has a much brighter rose top note and is fruitier and richer on dry out as compared with the same mixture without the composition of matter containing the 3-methyl-1-phenyl-pentanol-5 and the damascenone.

EXAMPLE II

Preparation of a Soap Composition

100 Grams of soap chips and prepared according to Example V of U.S. Pat. No. 4,058,490, issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dru dried. The resulting solid actives are then blended in a chip mixer with 10 lbs. water, 0.2 lb. titanium hydroxide"
are mixed with one gram of the perfume composition of Example I until a substantially homogeneous composition is obtained. The perfumed soap composition manifests an excellent fruity, rose character with green, earthy notes.

EXAMPLE III

Preparation of a Detergent Composition

A total of 100 grams of detergent powder prepared according to U.S. Pat. No. 4,058,472 and containing 5% by weight of the sodium salts of a mixture of sulfonated $C_{14}$-$C_{18}$ alkyl catechol as a surface active component, the mixture being 60 parts by weight of mono-$C_{14}$-$C_{18}$ alkyl catechol, 35% sodium tetrapyrrole phosphate, 30% of sodium carboxymethylcellulose and 7% of starch is mixed with 0.15 grams of the perfume composition of Example I, until a substantially homogeneous composition is obtained. This composition has an excellent fruity, rose aroma with earthy, green notes.

EXAMPLE IV

Prefumed Liquid Detergent

Concentrated liquid detergent each with a fruity, rosey aroma are prepared containing 0.10%, 0.15% and 0.20% of a mixture of damascenone and 3-methyl-1-phenyl-pentanol-5 in a weight ratio of 1:0.1 of 3-methyl-1-phenyl-pentanol-5:damascenone. They are prepared by adding and homogeneously mixing the appropriate quantity of a mixture of damascenone and 3-methyl-1-phenyl-pentanol-5 in the liquid detergent. The detergents all possess a fruity, rosey fragrance, the intensity increasing with greater concentrations of mixture of damascenone and 3-methyl-1-phenyl-pentanol-5.

EXAMPLE V

Preparation of a Cologne and Handkerchief Perfume

The composition of Example I is incorporated in a cologne at a concentration of 2.5% in 85% aqueous ethanol; and into a handkerchief perfume at a concentration of 20% (in 95% aqueous ethanol). The use of the mixture of damascenone and 3-methyl-1-phenyl-pentanol-5 in the composition of Example I affords a distinct and definite strong fruity, rose aroma with earthy and green notes to the handkerchief perfume and cologne.

EXAMPLE VI

Preparation of Soap Composition

100 Grams of soap chips are prepared according to Example V of U.S. Pat. No. 4,048,490 issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is drum dried. The resulting solid actives are then blended in a chip mixer with 10 lbs. water, 0.2 lb. titanium hydroxide"
are mixed with 1 gram of a mixture of damascenone and 3-methyl-1-phenyl-pentanol-5 where the ratio of damascenone:3-methyl-1-phenyl-pentanol-5 is 0.1:1, until a substantially homogeneous composition is obtained. The perfumed soap composition manifests an excellent rose aroma with woody, green and earthy notes and an excellent sweet top note.

EXAMPLE VII

Preparation of a Detergent Composition

A total of 100 g of a detergent powder prepared according to U.S. Pat. No. 4,058,472 and containing 5% by weight of the sodium salts of a mixture of sulfonated $C_{14}$-$C_{18}$ alkyl catechol as a surface active component, the mixture being 60 parts by weight of mono-$C_{14}$-$C_{18}$ alkyl catechol and 40 parts by weight of di-$C_{14}$-$C_{18}$ alkyl catechol, 35% sodium tetrapyrrole phosphate, 30% of sodium silicate, 20% of sodium carbonate, 3% of sodium carboxymethylcellulose and 7% of starch is mixed with 0.15 g of a mixture of damascenone and 3-methyl-1-phenyl-pentanol-5 (the ratio of damascenone: 3-methyl-1-phenyl-pentanol-5 being 0.2:1) until a substantially homogeneous composition is obtained. This composition has an excellent rose aroma with woody, green and earthy notes.

EXAMPLE VIII

Preparation of a Cologne and Handkerchief Perfume

A mixture of 1 part 3-methyl-1-phenyl-pentanol-5 and 2 parts damascenone is incorporated into a cologne at a concentration of 2.5% in 85% aqueous ethanol; and into a handkerchief perfume at a concentration of 20% (in 95% aqueous ethanol). A distinct and definite rose fragrance with woody, green and earthy top notes is imparted to the cologne and to the handkerchief perfume.

EXAMPLE IX

Preparation of a Cosmetic-Powder Composition

A cosmetic powder is prepared by mixing in a ball mill, 100 grams of talcum powder with 0.15 grams of a mixture consisting of 50% 3-methyl-1-phenyl-pentanol-5 and 50% damascenone. It has an excellent rose aroma with woody, green and earthy notes.

EXAMPLE X

ROSE FORMULATION

The following mixture is prepared:

| Ingredients | Parts by Weight |
| --- | --- |
| Rhodinol | 270.0 |
| Nerol | 90.0 |
| Linalool | 30.0 |
| Terpineol | 30.0 |
| Phenyl Ethyl Alcohol | 12.0 |
| Terpinenol | 5.0 |
| Linalyl Acetate | 1.5 |
| Citronellyl Acetate | 15.0 |
| Geranyl Acetate | 10.0 |
| Eugenol | 33.0 |
| Citral | 15.0 |
| Phenyl Ethyl Acetate | 20.0 |
| Rose Oxide | 8.0 |
| Guaiacol | 30.0 |
| 1-citronellal | 90.0 |
| Neryl Acetate | 3.0 |
| Clove Bud Oil | 1.0 |
| Cadinene | 2.0 |
| Guaiene | 1.0 |
| Gum Turpentine | 12.0 |
| Alpha-pinene | 1.0 |
| Myrcene | 5.0 |
| Limonene | 2.0 |
| p-cymene | 1.0 |
| | 687.5 |

To the foregoing formulation 30 parts by weight of a 0.1% solution of 3-methyl-1-phenyl-pentanol-5 in diethyl phthalate and 15 parts by weight of a 0.01% solution of beta-damascene in diethyl phthalate is added. The resultant mixture has a much brighter rose top note and is fruitier and richer on dry out as compared with the same mixture without the composition of matter containing the 3-methyl-1-phenyl-pentanol-5 and the beta-damascene.

EXAMPLE XI

Preparation of a Soap Composition

100 Grams of soap chips and prepared according to Example V of U.S. Pat. No. 4,058,490, issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dru dried. The resulting solid actives are then blended in a chip mixer with 10 lbs. water, 0.2 lb. titanium hydroxide"

are mixed with one gram of the perfume composition of Example I until a substantially homogeneous composition is obtained. The perfumed soap composition manifests an excellent fruity, rose character with green, earthy notes.

EXAMPLE XII

Preparation of a Detergent Composition

A total of 100 grams of detergent powder prepared according to U.S. Pat. No. 4,058,472 and containing 5% by weight of the sodium salts of a mixture of sulfonated $C_{14}$-$C_{18}$ alkyl catechol as a surface active component, the mixture being 60 parts by weight of mono-$C_{14}$-$C_{18}$ alkyl catechol, 35% sodium tetrapyrrole phosphate, 30% of sodium carboxymethylcellulose and 7% of starch is mixed with 0.15 grams of the perfume composition of Example I, until a substantially homogeneous composition is obtained. This composition has an excellent fruity, rose aroma with earthy, green notes.

EXAMPLE XIII

PREFUMED LIQUID DETERGENT

Concentrated liquid detergent each with a fruity, rosey aroma are prepared containing 0.10%, 0.15% and 0.20% of a mixture of beta-damascone and 3-methyl-1-phenyl-pentanol-5 in a weight ratio of 1:0.1 of 3-methyl-1-phenyl-pentanol-5:beta-damascone. They are prepared by adding and homogeneously mixing the appropriate quantity of a mixture of beta-damascone and 3-methyl-1-phenyl-pentanol-5 in the liquid detergent. The detergents all possess a fruity, rosey fragrance, the intensity increasing with greater concentrations of mixture of damascone and 3-methyl-1-phenyl-pentanol-5.

EXAMPLE XIV

Preparation of a Cologne and Handkerchief Perfume

The composition of Example I is incorporated in a cologne at a concentration of 2.5% in 85% aqueous ethanol; and into a handkerchief perfume at a concentration of 20% (in 95% aqueous ethanol). The use of the mixture of beta-damascone and 3-methyl-1-phenyl-pentanol-5 in the composition of Example I affords a distinct and definite strong fruity, rose aroma with earthy and green notes to the handkerchief perfume and cologne.

EXAMPLE XV

Preparation of Soap Composition

100 Grams of soap chips are prepared according to Example V of U.S. Pat. No. 4,058,490 issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is drum dried. The resulting solid actives are then blended in a chip mixer with 10 lbs. water, 0.2 lb. titanium hydroxide"

are mixed with 1 gram of a mixture of beta-damascone and 3-methyl-1-phenyl-pentanol-5 where the ratio of beta-damascone:3-methyl-1-phenyl-pentanol-5 is 0.1:1, until a substantially homogeneous composition is obtained. The perfumed soap composition manifests an excellent rose aroma with woody, green and earthy notes and an excellent sweet top note.

EXAMPLE XVI

Preparation of a Detergent Composition

A total of 100 g of a detergent powder prepared according to U.S. Pat. No. 4,058,472 and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ alkyl catechol, 35% sodium tetrapyrrole phosphate, 30% of sodium silicate, 20% of sodium carbonate, 3% of sodium carboxymethylcellulose and 7% of starch is mixed with 0.15 g of a mixture of beta-damascone and 3-methyl-1-phenyl-pentanol-5 (the ratio of beta-damascone:3-methyl-1-phenyl-pentanol-5 being 0.2:1) until a substantially homogeneous composition is obtained. This composition has an excellent rose aroma with woody, green and earthy notes.

EXAMPLE XVII

Preparation of a Cologne and Handkerchief Perfume

A mixture of 1 part 3-methyl-1-phenyl-pentanol-5 and 2 parts beta-damascone is incorporated into a cologne at a concentration of 2.5% in 85% aqueous ethanol; and into a handkerchief perfume at a concentration of 20% (in 95% aqueous ethanol). A distinct and definite rose fragrance with woody, green and earthy top notes is imparted to the cologne and to the handkerchief perfume.

EXAMPLE XVIII

Preparation of a Cosmetic-Powder Composition

A cosmetic powder is prepared by mixing in a ball mill, 100 grams of talcum powder with 0.15 grams of a mixture consisting of 50% 3-methyl-1-phenyl-pentanol-5 and 50% beta-damascone. It has an excellent rose aroma with woody, green and earthy notes.

EXAMPLE XIX

Rose Formulation

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenyl Ethyl Alcohol | 12.0 |
| Terpinenol | 5.0 |
| Linalyl Acetate | 1.5 |
| Citronellyl Acetate | 15.0 |
| Geranyl Acetate | 10.0 |
| Eugenol | 33.0 |
| Citral | 15.0 |
| Phenyl Ethyl Acetate | 20.0 |
| Rose Oxide | 8.0 |
| Guaiacol | 30.0 |
| 1-citronellal | 90.0 |
| Neryl Acetate | 3.0 |
| Clove Bud Oil | 1.0 |
| Cadinene | 2.0 |
| Guaiene | 1.0 |
| Gum Turpentine | 12.0 |
| Alpha-pinene | 1.0 |
| Myrcene | 5.0 |
| Limonene | 2.0 |
| p-cymene | 1.0 |
| | 687.5 |

To the foregoing formulation 30 parts by weight of a 0.1% solution of 3-methyl-1-phenyl-pentanol-5 in diethyl phthalate and 15 parts by weight of a 0.01% solution of cis, trans delta damascone in diethyl phthalate is added. The resultant mixture has a much brighter rose top note and is fruitier and richer on dry out as compared with the same mixture without the composition of matter containing the 3-methyl-1-phenyl-pentanol-5 and the cis, trans delta damascone.

EXAMPLE XX

Preparation of a Soap Composition

100 Grams of soap chips and prepared according to Example V of U.S. Pat. No. 4,058,490, issued on Nov. 15, 1977 as follows:

"The sodium salt of an equal mixture of $C_{10}$/$C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dru dried. The resulting solid actives are then blended in a chip mixer with 10 lbs. water, 0.2 lb. titanium hydroxide"

are mixed with one gram of the perfume composition of Example I until a substantially homogeneous composition is obtained. The perfumed soap composition manifests an excellent fruity, rose character with green, earthy notes.

EXAMPLE XXI

Preparation of a Detergent Composition

A total of 100 grams of detergent powder prepared according to U.S. Pat. No. 4,058,472 and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol, 35% sodium tetrapyrrole phosphate, 30% of sodium carboxymethylcellulose and 7% of starch is mixed with 0.15 grams of the perfume composition of Example I, until a substantially homogeneous composition is obtained. This composition has an excellent fruity, rose aroma with earthy, green notes.

EXAMPLE XXII

Prefumed Liquid Detergent

Concentrated liquid detergent each with a fruity, rosey aroma are prepared containing 0.10%, 0.15% and 0.20% of a mixture of cis, trans delta damascone and 3-methyl-1-phenyl-pentanol-5 in a weight ratio of 1:0.1 of 3-methyl-1-phenyl-pentanol-5:cis, trans delta damascone. They are prepared by adding and homogeneously mixing the appropriate quantity of a mixture of cis, trans delta damascone and 3-methyl-1-phenyl-pentanol-5 in the liquid detergent. The detergents all possess a fruity, rosey fragrance, the intensity increasing with greater concentrations of mixture of damascenone and 3-methyl-1-phenyl-pentanol-5.

EXAMPLE XXIII

Preparation of a Cologne and Handkerchief Perfume

The composition of Example I is incorporated in a cologne at a concentration of 2.5% in 85% aqueous ethanol; and into a handkerchief perfume at a concentration of 20% (in 95% aqueous ethanol). The use of the mixture of cis, trans delta damascone and 3-methyl-1-phenyl-pentanol-5 in the composition of Example I affords a distinct and definite strong fruity, rose aroma with earthy and green notes to the handkerchief perfume and cologne.

EXAMPLE XXIV

Preparation of Soap Composition

100 Grams of soap chips are prepared according to Example V of U.S. Pat. No. 4,058,490 issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is drum dried. The resulting solid actives are then blended in a chip mixer with 10 lbs. water, 0.2 lb. titanium hydroxide"
are mixed with 1 gram of a mixture of cis, trans delta damascone and 3-methyl-1-phenyl-pentanol-5 where the ratio of cis, trans delta damascone:3-methyl-1-phenyl-pentanol-5 is 0.1:1, until a substantially homogeneous composition is obtained. The perfumed soap composition manifests an excellent rose aroma with woody, green and earthy notes and an excellent sweet top note.

EXAMPLE XXV

Preparation of a Detergent Composition

A total of 100 g of a detergent powder prepared according to U.S. Pat. No. 4,058,472 and containing 5% by weight of the sodium salts of a mixture of sulfonated $C_{14}$-$C_{18}$ alkyl catechol as a surface active component, the mixture being 60 parts by weight of mono-$C_{14}$-$C_{18}$ alkyl catechol and 40 parts by weight of di-$C_{14}$-$C_{18}$ alkyl catechol, 35% sodium tetrapyrrole phosphate, 30% of sodium silicate, 20% of sodium carbonate, 3% of sodium carboxymethylcellulose and 7% of starch is mixed with 0.15 g of a mixture of cis, trans delta damascone and 3-methyl-1-phenyl-pentanol-5 (the ratio of cis, trans delta damascone:3-methyl-1-phenyl-pentanol-5 being 0.2:1) until a substantially homogeneous composition is obtained. This composition has an excellent rose aroma with woody, green and earthy notes.

EXAMPLE XXVI

Preparation of a Cologne and Handkerchief Perfume

A mixture of 1 part 3-methyl-1-phenyl-pentanol-5 and 2 parts cis, trans delta damascone is incorporated into a cologne at a concentration of 2.5% in 85% aqueous ethanol; and into a handkerchief perfume at a concentration of 20% (in 95% aqueous ethanol). A distinct and definite rose fragrance with woody, green and earthy top notes is imparted to the cologne and to the handkerchief perfume.

EXAMPLE XXVII

Preparation of a Cosmetic-Powder Composition

A cosmetic powder is prepared by mixing in a ball mill, 100 grams of talcum powder with 0.15 grams of a mixture consisting of 50% 3-methyl-1-phenyl-pentanol-5 and 50% cis, trans delta damascone. It has an excellent rose aroma with woody, green and earthy notes.

EXAMPLE XXVIII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolve Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of the mixture of 3-methyl-1-phenyl-pentanol-5 and cyclohexyl butenone derivatives of our invention as set forth in the Table I below and giving rise to the aroma nuances as set forth in said Table I below:

TABLE I

| DESCRIPTION OF MIXTURE | FRAGRANCE CHARACTERISTICS |
| --- | --- |
| Mixture containing .01% of beta damascenone in 3-methyl-1-phenyl-pentanol-5 | An intense rose aroma lasting for 3 weeks. |
| Mixture containing .2% beta-damascone in 3-methyl-1-phenyl-pentanol-5 | Interesting warm fruity rose aroma lasting for 3 weeks. |
| Mixture containing 0.5% trans, trans delta damascone in 3-methyl-1-phenyl pentanol-5 | Warm fruity, floral note with a rose body and a powerful rose top note lasting for 8 weeks. |

Fabric-softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table I above are imparted in a pleasant manner to the head space in the dryer on operation thereof using the said dryer added fabric softening nonwoven fabric.

What is claimed is:

1. A mixture consisting essentially of the 3-methyl-1-phenyl-pentanol-5 or stereoisomer thereof having a structure selected from the group consisting of:

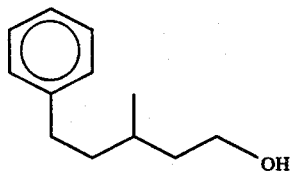

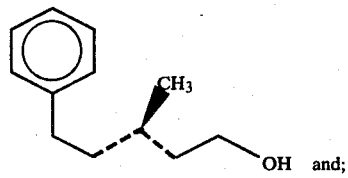 and;

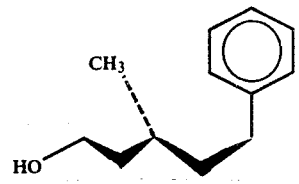

and intimately admixed therewith a cyclohexylbutenone derivative having the structure:

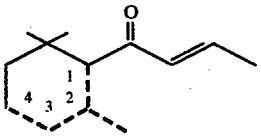

wherein one or two of the dashed lines is a carbon-carbon double bond and the other of the dashed lines is a carbon carbon single bond with the proviso that when two of the dashed lines are carbon-carbon doubles said carbon-carbon double bonds are conjugated and wherein the ratio of 3-methyl-1-phenyl-pentanol-5:cyclohexylbutenone derivative is from about $1:10^{-7}$ to about 1:0.1.

* * * * *